United States Patent [19]

Berg et al.

[11] Patent Number: 5,369,481
[45] Date of Patent: Nov. 29, 1994

[54] PORTABLE SPECTROPHOTOMETER

[75] Inventors: Bernard J. Berg, Kentwood; Thomas J. Boes, Grandville; Mark A. Cargill, Belding; Patrick S. Rood, Comstock Park, all of Mich.

[73] Assignee: X-Rite, Incorporated, Grandville, Mich.

[21] Appl. No.: 880,807

[22] Filed: May 8, 1992

[51] Int. Cl.⁵ .............................................. G01J 3/42
[52] U.S. Cl. .................................... 356/319; 356/236; 250/228
[58] Field of Search ................ 250/228; 356/236, 319, 356/416, 418, 419, 446, 445

[56] References Cited

U.S. PATENT DOCUMENTS

| | | | |
|---|---|---|---|
| 3,490,849 | 1/1971 | Hambleton . | |
| 3,956,201 | 5/1976 | Seiner | 356/236 |
| 4,093,991 | 6/1978 | Christie, Jr. et al. | 356/326 X |
| 4,540,281 | 9/1985 | Akiyama | 356/236 X |
| 4,915,500 | 4/1990 | Selkowitz | 356/221 |
| 4,968,143 | 11/1990 | Weston | 356/236 X |
| 4,995,727 | 2/1991 | Kawagoe et al. | 356/402 |

FOREIGN PATENT DOCUMENTS

| | | |
|---|---|---|
| 0099023 | 1/1984 | European Pat. Off. . |
| 0200918 | 11/1986 | European Pat. Off. . |
| 0306337 | 3/1989 | European Pat. Off. . |

OTHER PUBLICATIONS

The Measurement of Appearance, by Richard S. Hunter, published by John Wiley & Sons, Chapters 13, and 14, pp. 218-245, (1975).

*Primary Examiner*—Jill A. Johnston
*Attorney, Agent, or Firm*—Varnum. Riddering, Schmidt & Howlett

[57] ABSTRACT

A portable spectrophotometer includes a small-diameter optical sphere as well as optical detectors and signal processing and display circuitry which allows the instrument to be taken to an object to be measured and which provides a readout of color values at the portable instrument. The instrument is capable of providing specular-included and specular-excluded color readings simultaneously. The interior of the integrating sphere is coated with a highly reflective, color-absorbing material, and light from an incandescent lamp is diffused within the sphere prior to reaching the object to be measured. The sphere is provided with a first aperture which receives spectrally-included light and which is positioned to absorb a spectral component of the diffused source light. A second aperture positioned at a corresponding angular position with respect to the object measures specular-excluded light, excluding the specular component absorbed by the first aperture. Light detected from the first aperture is analyzed at a plurality of wavelengths obtained by the use of interference filters, and the light obtained from the second aperture is analyzed at one of the plurality of wavelengths. By appropriately combining the specular-included and specular-excluded at one wavelength, a value for the specular component is derived. Since this value is a theoretical constant, it is used to derive a specular-excluded reading from each of the specular-included readings at the different wavelengths.

4 Claims, 3 Drawing Sheets

PORTABLE SPECTROPHOTOMETER

BACKGROUND OF THE INVENTION

1. Field of the Invention

The invention relates to color measuring instruments and more particularly to spectrophotometers of a type that employ an integrating sphere in measuring light reflected from an object sample under test.

2. Prior Art

Spectrophotometers are instruments used to determine the color of an object under test and typically include a source of light projected onto the object, a photodetector detecting light reflected from the object sample and signal processing circuitry connected to the photodetector to compute curves or numerical values indicative of color. The general principles of construction and use of these instruments are well known and understood by those skilled in the art and are described in published texts such as the text by Richard S. Hunter entitled *The Measurement of Appearance*, John Wiley & Sons, 1975.

One known type of spectrophotometer uses an integrating sphere in which the light reflected from the object is integrated to obtain an average reading of the color over an exposed surface area of the object. Known integrating spheres can provide readings which represent "total" reflections or "diffuse-only" reflections. The total reflections include all reflections from the exposed object, including reflections from the surface and diffuse reflections from particles in the body of the object. The "diffuse-only" measurement is obtained by excluding the first surface reflections which are reflected at the specular angle and may be referred to as the specular component. Exclusion of the specular component eliminates the light contribution due to gloss, and the color values obtained from a specular-excluded reading are independent of the glossiness of the surface of the object under test.

The specular angle is equal and opposite to the angle of incidence of a source light beam projected onto the object under test. A typical angle for the source light beam in prior art arrangements is 8 degrees off the vertical centerline of the sphere. The specular-excluded reading is obtained in such a sphere by providing a light-absorbing area on the sphere at 8 degrees off the centerline and on the opposite side of the centerline from the light source. The absorbing spot may be created by a opening in the outer surface of the sphere with a dark area or black plug placed in the opening to absorb the specular component.

Prior art integrating spheres used in the photospectrometers are commonly quite large, for example, 6 to 8 inches in diameter. The size of the sphere is dictated to some extent by the diameter of the measuring opening adjacent to the object under test and the space in the sphere surface for a light source, the specular absorption area, and detectors, while allowing sufficient interior surface area for integrating action in the sphere. Because the prior art spheres are relatively large, and additional space is needed for lenses associated with the light source and detection and analysis or signal processing apparatus, the typical prior art photospectrometer is a bench unit which is awkward to move and objects to be tested must be brought over to the bench unit. The need for an accurate portable spectrophotometer is readily apparent. Portable spectrophotometer may, for example, be used to measure the color of paint on the wall of a large auditorium, on automobiles, bolts of textile, etc., without the need to move portions or sections of these objects to a bench photospectrometer. The problem in prior art systems is that no practical, small-diameter, integrating sphere has been available to measure both specular-included and specular-excluded sample effects on a relatively large sample area.

SUMMARY OF THE INVENTION

These and other problems of the prior art are solved in accordance with this invention by means of a spectrophotometer employing an integrating sphere comprising a source of light which is diffused within the sphere, and the sphere provides diffused source light to the sample. A first sensor aperture in the interior wall of the sphere is directed at the sample at a predetermined angle from the vertical centerline of the sphere and detects total light reflected from the sample. A second sensor aperture, directed at a portion of the interior wall of the sphere provides a reading representing the source of the light projected onto the sample. Analysis of the light detected from these two apertures allows one to compute the light reflected from the object under test. A third sensor aperture is incorporated in the wall of the sphere at a position from the vertical centerline of the sphere which is opposite to the position of the first aperture and at an angle from that centerline which is equal in magnitude to the predetermined angle of the first aperture.

The first aperture presents a relatively large light-absorbing area. Hence, the light detected by the third aperture represents the light reflected from the sample and integrated in the sphere minus a specular component absorbed at the first aperture and represents specular-excluded light. The third aperture has minimal light-absorbing characteristics, and therefore emits a specular component of light to the sample which is reflected to the first aperture. Hence specular-included light is sensed at the first aperture.

In accordance with one aspect of the invention, a sphere spectrophotometer comprises at least two sensor apertures and detects both specular-included and specular-excluded light reflected from an object under test.

In accordance with another aspect of the invention, a sphere photospectrometer employs a non-directed light source not requiring lenses and monochromators which can be inserted in a relatively small opening in the sphere at any desired position. As a consequence, the size of the sphere is reduced to where it is readily portable.

Advantageously, the spectrophotometer sphere can be made to be less than 3 inches in diameter, and the spectrophotometer can be readily constructed as a portable, hand-held device.

In accordance with another aspect of the invention, the specular component can be computed from the specular-included and specular-excluded readings at a defined wavelength, and the value of the specular component, which is known to be a theoretical constant for all wavelength individual spectrum, can be used to derive a specular excluded value for other wavelengths in the visible spectrum.

BRIEF DESCRIPTION OF THE DRAWING

An embodiment of the invention is described below with reference to drawing in which.

DETAILED DESCRIPTION

Figure 1:
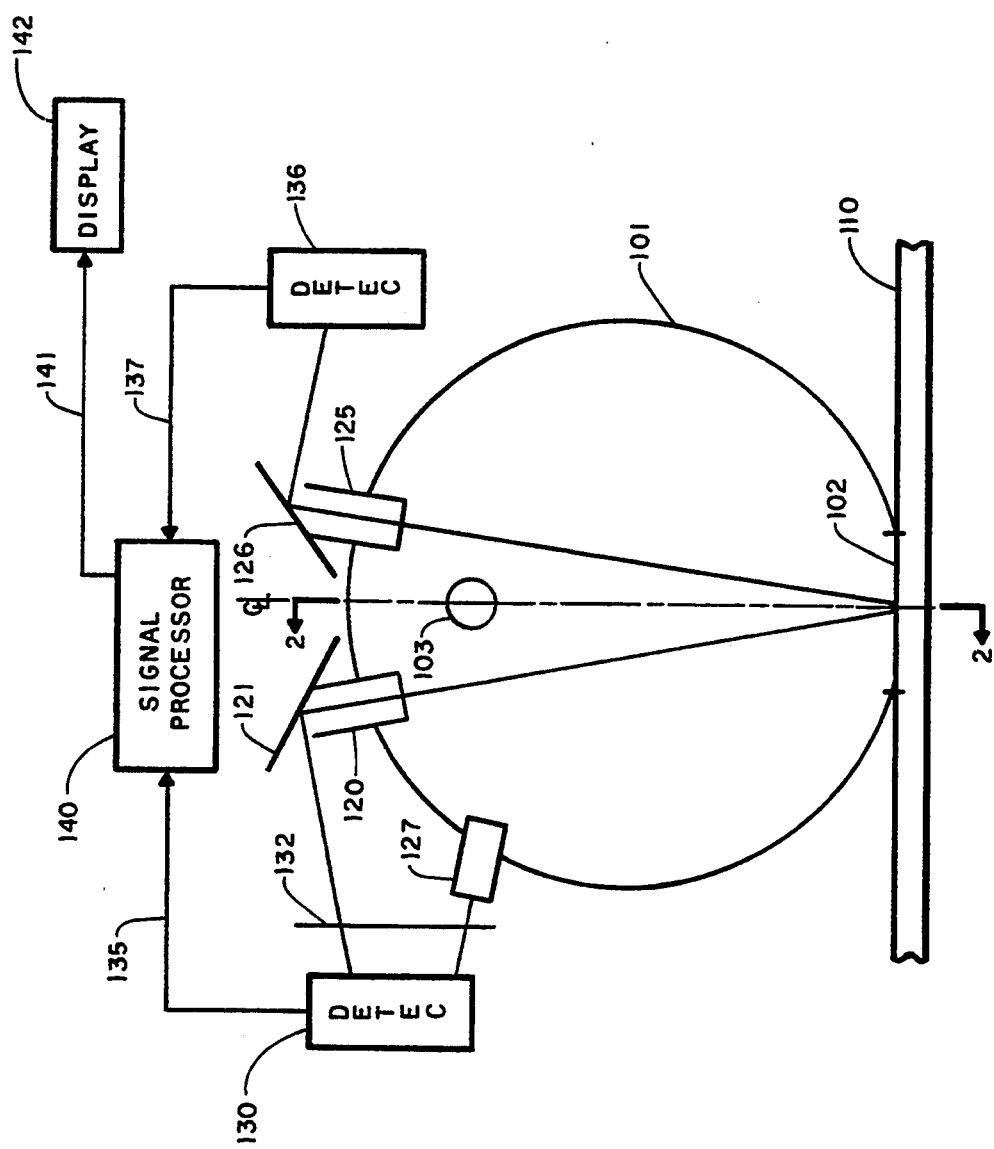
FIG. 1 is a diagrammatic representation of a spectrophotometer embodying the principles of the invention.

FIG. 1 is a diagrammatic representation of a spectrophotometer embodying the principles of the invention. The basic spectrophotometer system includes an integrating sphere 101 having an opening 102 to expose an object sample to light. A lamp 103 provides light which is diffused by reflection within the sphere 101, and components of this diffused light are projected onto an object sample 110 which is to be tested. A primary aperture 120 is directed to the object sample 110 and receives light reflected from the object sample. Aperture 120 is located adjacent the vertical centerline of the sphere and along a line extending at a predetermined angle from the centerline.

It is well understood that a portion of the light incident on the sample is reflected from the surface of the sample as specular light, and a portion of the light is diffused in the sample and reflected as diffuse light. The specular light is reflected from the surface of the sample at an angle equal to the incident angle and to a location on the internal surface of the sphere which is readily ascertainable. The diffuse and specular light components reflected from the object strike the interior surface of the sphere which serves to provide integrated light. Since the light received at aperture 120 includes both diffuse light and the specular component surface reflected light, it represents total reflected light. Hence, it is referred to as specular-included light. It is also referred to herein as the "Spec-in" light.

The lamp 103 may be an incandescent lamp which is pulsed in a customary manner to heat the lamp filament to a high temperature, e.g., greater than 3,000 degrees kelvin. The interior of the sphere may be coated with a highly reflective inner coating which is preferably spectrally flat and may be a color-correcting, absorbing material in order to reduce the red and green color elements in the light to obtain a higher color temperature source. The diffused light from the sphere illuminating the sample 110 through the opening 102 includes at least one light component which strikes the surface of the object sample at an angle such that it has an angle of reflection which coincides with the angle of the primary aperture 120. Thus, the angle of aperture 120 is the specular angle for the corresponding component of the source light. The aperture 120 comprises an aperture structure which has a blackened appearance to absorb the specular component reflected from the object sample along the aforementioned angle. A secondary aperture 125 is positioned opposite aperture 120 and at the same angle from the vertical centerline of the sphere. Thus, it is aligned with the angle of incidence of the particular light component which has a specular angle aligned with aperture 120. By way of example, apertures 120 and 125 may be displaced from the vertical centerline by 8 degrees. Since the specular component of at least one component of the diffused source light aligned with aperture 125 is absorbed in aperture 120, the aperture 125 receives only diffuse light from the object sample with respect to the one particular component of source light. Accordingly, with respect to that component of source light, the light received at aperture 125 represents specular excluded light, also referred to herein as "Spec-ex." The specular component of incident light may be defined as the difference between Spec-in and Spec-ex, which difference is a theoretical constant over all wavelengths. Therefore, having derived a value for the specular component for one wavelength, the Spec-ex reading can be readily derived from the value of the specular component and the Spec-in reading.

The diagrammatic representation of FIG. 1 shows a third aperture 127. Aperture 127 is directed to the opposite inner wall of the sphere and provides a reading of the source light which is equivalent to the source light incident on the object sample 110. Since the light of lamp 103 is diffused throughout the sphere, apertures 120 and 125 are collimated to reject source light and receive only light reflected from the object sample 110. The reading obtained via aperture 127, which is essentially source light only, may be used to compensate for variations in diffuse light striking the sample and changing the readings obtained via apertures 120 and 125, in order to obtain a more accurate reading of the light reflected from the sample.

In one illustrative embodiment of the invention, the light received at aperture 120 is reflected by means of a mirror 121 and transmitted to a detector 130 via a shutter mechanism 132. Furthermore, the light incident on aperture 127 is also directed to the detector 130 via the shutter apparatus 132. An electrical output signal generated by detector 130 is transmitted to a signal processor 140 by means of an interconnecting conductor 135. The shutter apparatus 132 alternately conducts light from apertures 120 and 127 to the detector 130 at a predetermined periodic rate, and the output signals of the detector are discriminated by the signal processor 140. Reflected light incident on aperture 125 is reflected by means of a mirror 126 and may be transmitted to a second detector 136 connected to the signal processor 140 via conductor 137. The signal processor 140 may be a well-known microprocessor which is programmed to provide a human readable output on a well-known display device 142 connected to the signal processor 140 by conductor 141.

Detectors 130 and 136 may be a single multi-cell photodetector. The light received at aperture 120 will be analyzed by the signal processor 140 for energy level at a plurality of wavelengths in the visible spectrum. In this illustrative embodiment, the received light is transmitted from apertures 120 and 127 via a bundle of 16 fibers terminating on a broadband filter comprising 16 interference filter elements in detector 130. Each filter element is designed to pass only light of a selected wavelength in the visible spectrum, for example, wavelengths at 400, 420, 440 . . . nanometers up to 700 nanometers. The light incident on aperture 125 is of interest primarily for purpose of identifying the specular component and employs only a single filter.

Sixteen electrical signals generated from the 16 filter elements are used by the signal processing circuitry to analyze the detected light and to display output values or curve representative of the color of the object sample. The specifics of computing color values are well known and may be expressed in terms of standardized X, Y, and Z parameter. By means of the shutter apparatus 132, the 16 primary filter elements of detector 130 are alternately exposed to light from the apertures 120 and 127. Accordingly, the signal processor alternately analyzes the source light and the specular-included reflected light at each of the selected wavelength, and the specular-included values for the object sample can be readily computed.

A 17th output value representing the specular-excluded or Spec-ex values of light received at aperture 125 is analyzed at a selected visible spectrum wavelength, e.g., 420 nanometers. Since the specular component at any wavelength is defined as the difference between Spec-in and Spec-ex at that wavelength, the specular component can be readily computed. Since the specular component is a theoretical constant for all wavelengths, and since the Spec-in value has been computed for each of 16 wavelengths, the Spec-ex can also be readily computed for each of the 16 wavelengths. Accordingly, both Spec-in and Spec-ex values can be provided for object under test without the need for separate readings.

The light value obtained from aperture 125, in addition to being used in derivation of the specular component, may also be used in the derivation of values for source light together with the light values obtained from aperture 127 in order to provide a more accurate value for source light.

It will be understood by those skilled in the art that the accuracy of the computed magnitude of the specular component may be influenced by the spectral properties of the optical components, at different wavelengths. Hence, in order to obtain greater accuracy, the value of the specular component may be improved by compensating for the spectral properties of the various components associated with the measurement. In the system of this invention, the spectral properties of each of the optical components of the system are measured at each of 16 different wavelengths in the visible range, e.g., at equal intervals between 400 to 700 nanometers, and a compensation value for each measured wavelength is recorded in tables stored in the memory of the signal processor 140. These tables are then subsequently used in the computation of the specular component in the signal processor 140.

Figure 2:
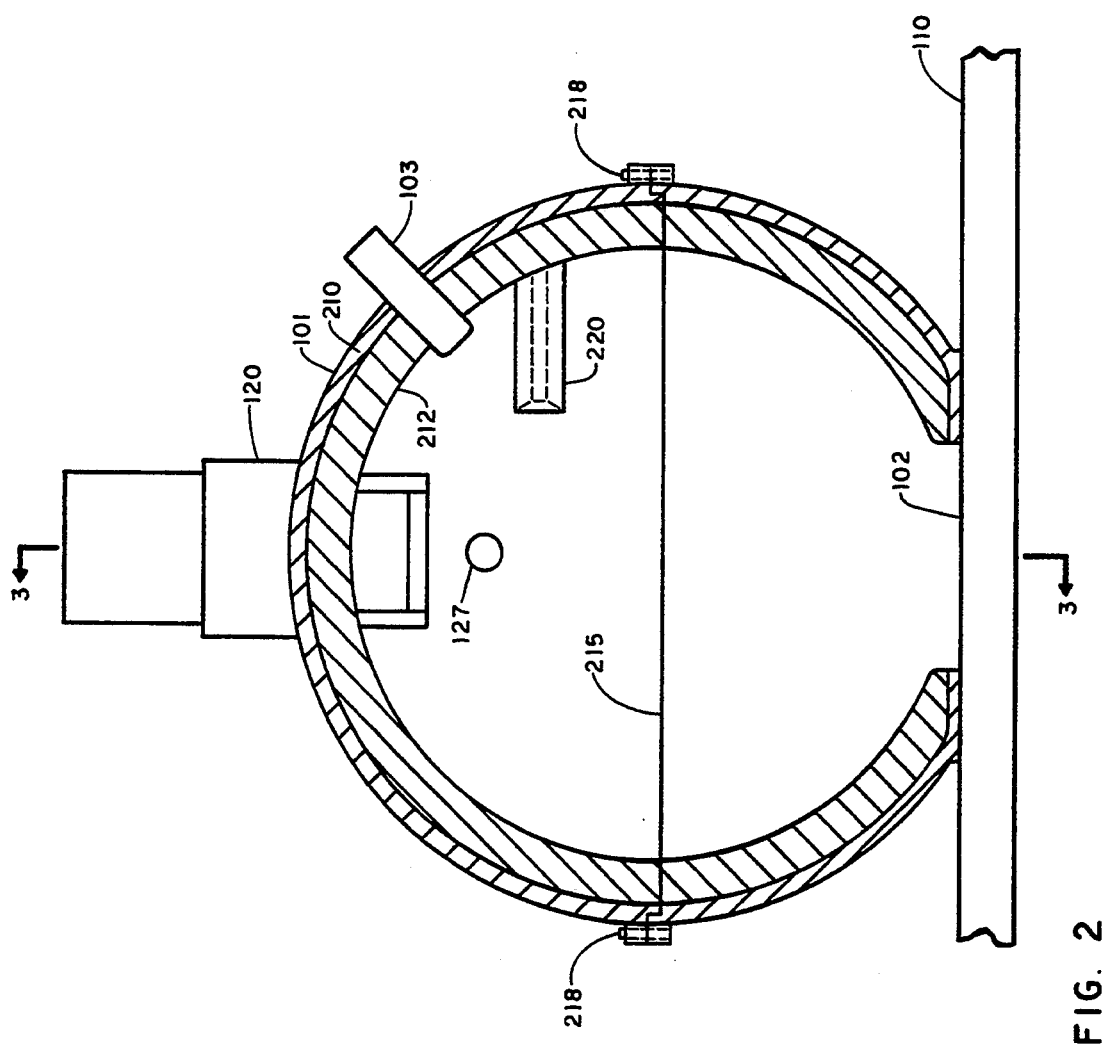
FIG. 2 is an enlarged cross-sectional view along line 2—2 of FIG. 1.

FIG. 2 is an enlarged cross-sectional view of the sphere 101 along line 2—2 of FIG. 1. The sphere 101 consists of an outer metallic layer 210 and an inner layer 212. In one illustrative embodiment, the inner diameter of the sphere is approximately 2.3 inches, and the outer diameter is approximately 2.5 inches. The inner layer 212 is a color-correcting, absorptive material and may, for example, be commercially available SPECTRALON or halon with a reflection factor of on the order of 0.99. The sphere 101 is split along the horizontal line to 15 to facilitate construction. The inner shell may be machined to properly fit within the outer shell and inserted in the outer shell while it is split apart. The two halves of the sphere may be appropriately secured by standard fasteners 218. The sphere 101 is provided with an interior baffle 220 fastened to the wall of the sphere. The baffle aids in diffusing the light from the lamp 103 and prevents the lamp from directly illuminating the object sample 110 through opening 102.

Figure 3:
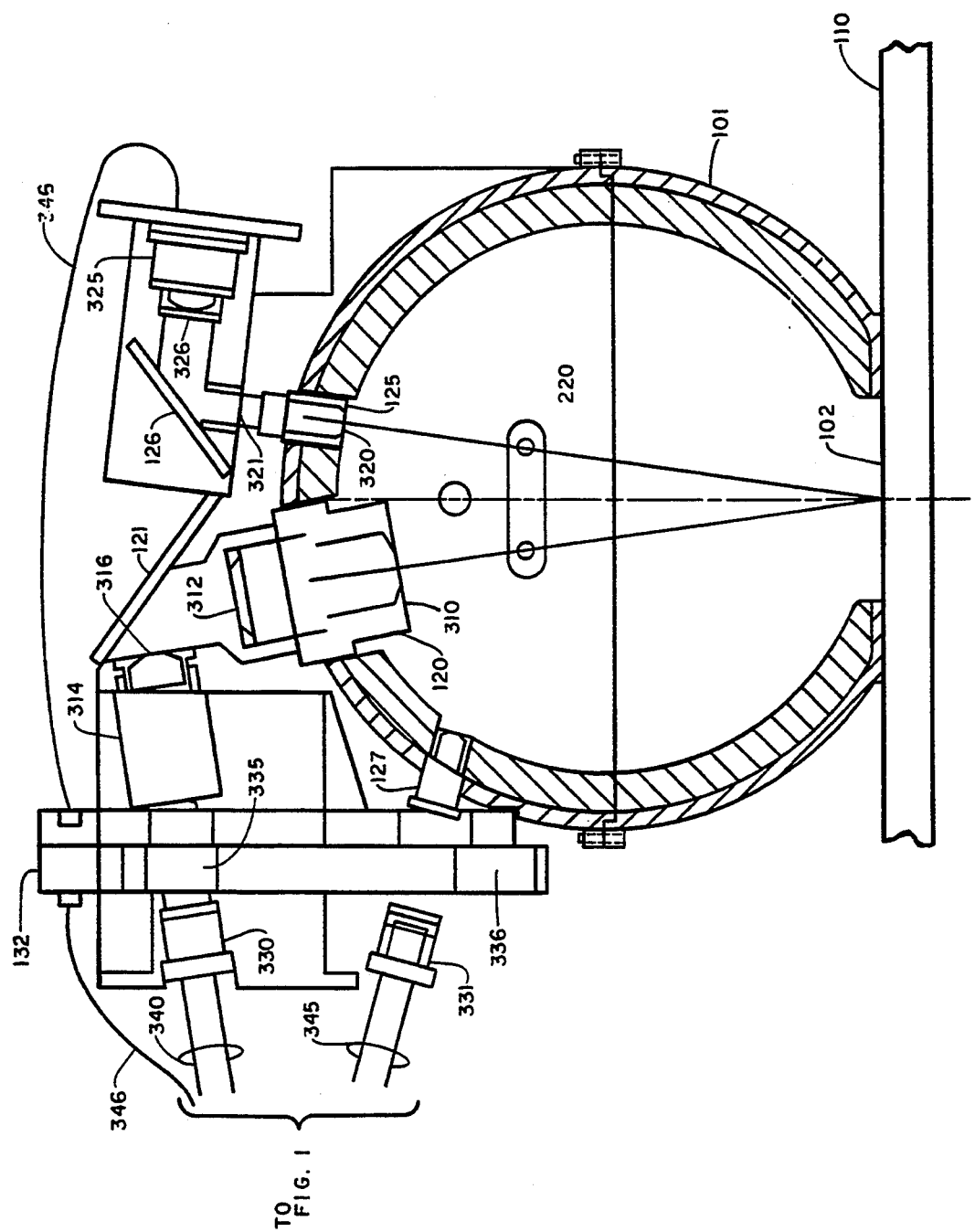
FIG. 3 is an enlarged cross-sectional view along line 3—3 of FIG. 2.

FIG. 3 is a enlarged cross section of the sphere 101 shown diagrammatically in FIG. 1 and along the centerline 3—3 of FIG. 2. In this illustrative embodiment, the aperture structure 120 is provided with an aperture 310 of approximately 0.3 inches in diameter at the end extending into the sphere and at the opposite end with an aperture 312 of approximately 0.2 inches in diameter. Aperture structure 120 may comprise a collimating lens. A further collimating lens 314, provided with an aperture 316, is aligned to receive light reflected from the mirror 121 and is provided with an aperture 316 at the end adjacent to the mirror of approximately 0.15 inches in diameter. The external surfaces of aperture structure 120 exposed to the interior are blackened to better absorb the specular component and provide a more accurate reading for the Spec-ex value. The aperture structure 125 is provided with an aperture 320 of approximately 0.075 inches diameter at the end exposed to the interior of the sphere and is provided with an aperture 321, of the same diameter, at the opposite end. Aperture structure 125 may comprise a collimating lens. An additional lens 325 is aligned to receive light reflected from the mirror 126 and is provided with an opening 326 adjacent to the mirror 126 and having an aperture of approximately 0.11 inches in diameter. The aperture 125 has intentionally been made comparatively small to avoid a significant adverse effect on the Spec-in reading. Furthermore, aperture 125 may be coated to have a reflection factor which is commensurate with the average reflection factor of the sphere to further reduce the effect of this aperture.

Additional collimating lenses 330, 331 are provided to transmit the light via two 16-fiber optical fiber bundles 340 and 345, respectively, to the detector 130, shown in FIG. 1. The optical output of lens 325 is transmitted via optical fiber 346 to detector 136 shown in FIG. 1. As mentioned earlier, detectors 130 and 136 may be a single multi-cell detector.

The shutter apparatus 132 may be a sliding device having openings 335, 336 which may be shuttled between a position in which opening 335 is aligned to transmit light and opening 336 is not and vice versa. Alternatively, a rotating shutter may be employed which allows the passage of light from only one of the two sensors 120, 127 at any one time. The shutter device may be operated by an electric motor (not shown) at a predetermined rate or operated on the control of the signal processor 140 in a standard fashion.

It will be understood that the embodiment described herein is only illustrative of the principles of the invention and various other embodiments may be devised by those skilled in the art without departing from the spirit and scope of the invention as claimed herein.

What we claim is:

1. Spectrophotometer apparatus for measuring color of an object under test, comprising:

an integrating sphere;

a test opening in said sphere providing access to said object under test;

a light source providing diffused source light projected through said test opening and comprising a lamp providing multidirectional light output such that at least a portion of light provided by said lamp is reflected from interior surfaces of said sphere, said lamp extending at least partially into said sphere and wherein said sphere further comprises a deflecting baffle mounted internal to said sphere adjacent said lamp and deflecting light from said lamp;

a first sensor aperture disposed in said sphere and directed toward said test opening along a line extending at a predetermined angle from a vertical centerline of said sphere detecting all light reflected from said test opening, including at least one surface reflected specular light component reflected from said opening along said line extending at said predetermined angle;

a second sensor aperture disposed in said sphere at a position opposite said centerline from said first sensor and aligned along a line extending at said predetermined angle from said centerline detecting light reflected from said test opening exclusive of said specular light component;

a plurality of sensors optically connected to said apertures; and a signal processor connected to said sensors for combining readings of diffuse light and said at least one surface reflected specular light component received at said first sensor aperture with diffuse light excluding said reflected specular light component received at said second sensor aperture.

2. Spectrophotometer apparatus for measuring color of an object under test, comprising:

an integrating sphere;

a test opening in said sphere providing access to said object under test;

a light source providing diffused source light projected through said test opening;

a first sensor aperture disposed in said sphere and directed toward said test opening along a line extending at a predetermined angle from a vertical centerline of said sphere detecting all light reflected from said test opening, including at least one surface reflected specular light component reflected from said opening along said line extending at said predetermined angle;

a second sensor aperture disposed in said sphere at a position opposite said centerline from said first sensor and aligned along a line extending at said predetermined angle from said centerline detecting light reflected from said test opening exclusive of said specular light component;

first and second sensors optically connected to said first and second apertures, respectively;

a third sensor directed to an area of an interior surface area of said sphere and providing an output indicative of said source light in said sphere; and a signal processor connected to said sensors for combining readings of diffuse light and said at least one surface reflected specular light component received at said first sensor aperture with diffuse light excluding said reflected specular light component received at said second sensor aperture.

3. Spectrophotometer apparatus for measuring color of an object under test, comprising:

an integrating sphere;

a test opening in said sphere providing access to said object under test;

a light source providing diffused source light projected through said test opening;

a first sensor aperture disposed in said sphere and directed toward said test opening along a line extending at a predetermined angle from a vertical centerline of said sphere detecting all light reflected from said test opening, including at least one surface reflected specular light component reflected from said opening along said line extending at said predetermined angle; and a second sensor aperture disposed in said sphere at a position opposite said centerline from said first sensor and aligned along a line extending at said predetermined angle from said centerline detecting light reflected from said test opening exclusive of said specular light component;

said first sensor aperture comprising a light absorbing aperture and said second sensor aperture having a reflection factor corresponding to said average reflection factor of said sphere;

a plurality of sensors optically connected to said apertures; and a signal processor connected to said sensors for combining readings of diffuse light and said at least one surface reflected specular light component received at said first sensor aperture with diffuse light excluding said reflected specular light component received at said second sensor aperture.

4. In a spectrophotometer, a method of measuring diffuse light and reflected specular light from an object under test, said method comprising the steps of:

exposing a selected surface area of said object under test to diffused source light;

measuring specular-included total integrated light including surface reflected light reflected from said selected exposed area from a first position disposed on one side of a vertical centerline extending through said selected exposed area and along a line extending along a predetermined angle from said centerline;

measuring specular-excluded integrated light reflected from said exposed area from a second position opposite said centerline from said first position and along a line extending at said predetermined angle from said centerline and excluding at least one surface reflected specular component of said light reflected from said selected exposed area to said first position; and combining measurements taken from said first and said second positions to derive an output value representative of said specular component;

said step of measuring light from said first position comprising measuring said specular-included light at a plurality of wavelengths and said step of measuring from said second position comprises measuring said specular-excluded light for at least one wavelength of said plurality of wavelengths and further comprising the step of deriving a specular component value for said at least one wavelength from results derived from said measuring steps and the step of using said specular component value to derive a specular-excluded value for a plurality of said wavelengths.

* * * * *